(12) United States Patent  
Stibich et al.

(10) Patent No.: US 8,816,301 B2
(45) Date of Patent: Aug. 26, 2014

(54) LAMP AND REFLECTOR ARRANGEMENTS FOR APPARATUSES WITH MULTIPLE GERMICIDAL LAMPS

(71) Applicant: Xenex Healthcare Services, LLC, Austin, TX (US)

(72) Inventors: Mark A. Stibich, Houston, TX (US); Paul P. Froutan, Katy, TX (US); James R. Ogle, Sanford, MI (US); Troy D. Smith, Houston, TX (US)

(73) Assignee: Xenex Healthcare Services, LLC, San Antonio, TX (US)

( * ) Notice: Subject to any disclaimer, the term of this patent is extended or adjusted under 35 U.S.C. 154(b) by 0 days.

(21) Appl. No.: 13/708,208

(22) Filed: Dec. 7, 2012

(65) Prior Publication Data

US 2014/0158917 A1 Jun. 12, 2014

(51) Int. Cl.
*A61L 2/10* (2006.01)

(52) U.S. Cl.
USPC . 250/455.11; 250/428; 250/436; 250/453.11; 250/454.11; 422/22; 422/24

(58) Field of Classification Search
USPC .......... 250/428, 432 R, 436, 453.11, 454.11, 250/455.11; 422/22, 24
See application file for complete search history.

(56) References Cited

U.S. PATENT DOCUMENTS

| | | |
|---|---|---|
| 2,182,732 A | 12/1927 | Meyer et al. |
| 2,382,939 A | 6/1944 | Koch |
| 2,392,095 A | 1/1946 | Lemmers |
| 2,615,120 A | 12/1949 | Macksoud |
| 3,418,069 A | 12/1968 | Decupper |
| 4,005,135 A | 1/1977 | Helding |
| 4,229,658 A | 10/1980 | Gonser |
| 4,896,042 A | 1/1990 | Humphreys |
| 5,144,146 A | 9/1992 | Wekhof |
| 5,220,734 A | 6/1993 | Carver |
| 5,221,139 A | 6/1993 | Belfer |

(Continued)

FOREIGN PATENT DOCUMENTS

| | | |
|---|---|---|
| CN | 87203475 | 8/1988 |
| CN | 2678651 | 2/2005 |

(Continued)

OTHER PUBLICATIONS

Partial International Search Report, PCT/US2013/065184, mailed Jan. 31, 2014.

*Primary Examiner* — Nicole Ippolito
(74) *Attorney, Agent, or Firm* — Mollie E. Lettang; Daffer McDaniel LLP

(57) ABSTRACT

Germicidal lamp apparatuses are provided with lamps disposed between upper and lower bases of a support structure. In some embodiments, a longitudinal axis of a lamp is at an acute angle greater than 0° relative to a region of the lower base between the lamp and another lamp. In addition, the longitudinal axis of the other lamp is at either a right angle or an obtuse angle relative to said region. Other embodiments of apparatuses include a reflector system disposed between the upper and lower bases which is common to the lamps and which includes a reflector with slanted peripheral edge. Other germicidal lamp apparatuses are provided which include a reflector with multiple sections each contoured to manipulate directionality of light emitted from a subset of lamps. In such cases, the apparatuses are configured to move the reflector and/or collectively move the lamps during illumination of the lamps.

26 Claims, 5 Drawing Sheets

(56) References Cited

U.S. PATENT DOCUMENTS

| | | |
|---|---|---|
| 5,344,433 A | 9/1994 | Talmore |
| 5,373,430 A | 12/1994 | McDermott |
| 6,203,060 B1 | 3/2001 | Cech et al. |
| 6,242,753 B1 | 6/2001 | Sakurai |
| 6,465,799 B1 | 10/2002 | Kimble et al. |
| 6,493,087 B1 | 12/2002 | Fabinski et al. |
| 6,539,727 B1 | 4/2003 | Burnett |
| 6,566,659 B1 | 5/2003 | Clark et al. |
| 6,656,424 B1 | 12/2003 | Deal |
| 6,759,664 B2 | 7/2004 | Thompson et al. |
| 6,774,382 B2 | 8/2004 | Yoshida |
| 6,911,177 B2 | 6/2005 | Deal |
| 6,932,494 B1 | 8/2005 | Burnett et al. |
| 6,962,239 B2 | 11/2005 | Shikai et al. |
| 7,175,806 B2 | 2/2007 | Deal et al. |
| 7,329,026 B1 | 2/2008 | Hayman et al. |
| 7,459,694 B2 | 12/2008 | Scheir et al. |
| 7,476,006 B2 | 1/2009 | Hinds |
| 7,498,004 B2 | 3/2009 | Saccomanno |
| 8,038,949 B2 | 10/2011 | Horne et al. |
| 8,142,713 B2 | 3/2012 | Gordon |
| 8,193,515 B2 | 6/2012 | Kreitenberg |
| 8,203,126 B2 | 6/2012 | Rocha-Alvarez et al. |
| 2003/0085631 A1 | 5/2003 | Cech et al. |
| 2003/0086821 A1 | 5/2003 | Matthews |
| 2003/0137834 A1 | 7/2003 | Jigamian et al. |
| 2004/0024278 A1 | 2/2004 | Megerle |
| 2004/0052702 A1 | 3/2004 | Shuman et al. |
| 2004/0140782 A1 | 7/2004 | Okabe et al. |
| 2004/0175290 A1 | 9/2004 | Scheir et al. |
| 2005/0025662 A1 | 2/2005 | Lestician |
| 2005/0058013 A1 | 3/2005 | Warf et al. |
| 2005/0133740 A1 | 6/2005 | Gardner |
| 2005/0151937 A1 | 7/2005 | Sugitani |
| 2006/0045817 A1* | 3/2006 | Horne et al. ......... 422/121 |
| 2006/0244403 A1 | 11/2006 | Christensson et al. |
| 2006/0261291 A1 | 11/2006 | Gardner |
| 2006/0284109 A1 | 12/2006 | Scheir et al. |
| 2007/0140893 A1 | 6/2007 | McVey et al. |
| 2007/0188113 A1 | 8/2007 | Okamoto |
| 2007/0231189 A1 | 10/2007 | Jung et al. |
| 2007/0231204 A1 | 10/2007 | Hyde et al. |
| 2008/0056933 A1 | 3/2008 | Moore et al. |
| 2008/0213128 A1 | 9/2008 | Rudy et al. |
| 2008/0253941 A1 | 10/2008 | Wichers et al. |
| 2008/0260601 A1 | 10/2008 | Lyon |
| 2009/0123343 A1 | 5/2009 | Kwiatkowski |
| 2009/0129974 A1 | 5/2009 | McEllen |
| 2009/0191100 A1 | 7/2009 | Deal |
| 2009/0217547 A1 | 9/2009 | Kim et al. |
| 2009/0314308 A1 | 12/2009 | Kim et al. |
| 2009/0323181 A1 | 12/2009 | Andrews et al. |
| 2010/0026726 A1 | 2/2010 | Fujii |
| 2010/0044319 A1 | 2/2010 | Engel et al. |
| 2010/0183476 A1 | 7/2010 | Lu |
| 2011/0002821 A1 | 1/2011 | Hyde et al. |
| 2011/0054574 A1 | 3/2011 | Felix |
| 2011/0215261 A1 | 9/2011 | Lyslo et al. |
| 2012/0047763 A1 | 3/2012 | Abramovich et al. |
| 2012/0223216 A1 | 9/2012 | Flaherty et al. |

FOREIGN PATENT DOCUMENTS

| | | |
|---|---|---|
| CN | 201755324 | 3/2011 |
| DE | 149020 | 6/1981 |
| EP | 0566238 | 10/1993 |
| EP | 2174670 | 4/2010 |
| EP | 2172097 | 7/2010 |
| EP | 2314802 | 4/2011 |
| GB | 2452341 | 3/2009 |
| JP | 57-164062 | 10/1982 |
| JP | 60-63107 | 4/1985 |
| JP | 6-63107 | 3/1994 |
| JP | 2003-135581 | 5/2003 |
| JP | 2010-276737 | 12/2010 |
| KR | 20-2011-0003951 | 4/2011 |
| WO | 94/06482 | 3/1994 |
| WO | 02/058744 | 8/2002 |
| WO | 2007/020282 | 2/2007 |
| WO | 2007/089312 | 8/2007 |
| WO | 2012/142427 | 10/2012 |

* cited by examiner

LAMP AND REFLECTOR ARRANGEMENTS FOR APPARATUSES WITH MULTIPLE GERMICIDAL LAMPS

BACKGROUND OF THE INVENTION

1. Field of the Invention

This invention generally relates to germicidal lamp systems and apparatuses and, more specifically, to lamp and reflector arrangements for lamp systems and apparatuses having a plurality of germicidal lamps.

2. Description of the Related Art

The following descriptions and examples are not admitted to be prior art by virtue of their inclusion within this section.

Pathogenic microorganisms are becoming increasingly resistant to antimicrobial pharmaceuticals and, thus, treating germicidal infections are getting more difficult to treat. As a consequence, thorough disinfection of surfaces and objects is becoming increasingly important as a preventive measure against exposure. Examples of disinfection applications include sterilization of surgical tools, food and pharmaceutical packaging, decontamination of fluid streams, and area/room decontamination (e.g., disinfection of surfaces and objects in hospital rooms or for agricultural operations). It is known that irradiation of ultraviolet (UV) light in the spectrum between approximately 200 nm and approximately 320 nm is effective in deactivating and, in some cases, killing microorganisms, giving cause for the use of ultraviolet light technology for disinfection applications. Within the past few years, violet wavelengths of visible light in the spectrum between approximately 380 nm and approximately 420 nm and particularly centered on 405 nm (known as high-intensity narrow-spectrum (HINS) light) have been proven to be effective in deactivating and, in some cases, killing microorganisms. Thus, the use of HINS technology is being contemplated as an additional or alternative manner for disinfection applications.

Although different types of lamps have been investigated to provide UV light for different disinfection applications, little has been done to improve the propagation of UV light (i.e., distance and angle of incidence on a target object) in disinfection apparatuses. A reason for such a lack of advancement is that many disinfection apparatuses having UV lamps, such as food sterilization and single object disinfection devices, are configured to treat items placed in close proximity and in direct alignment with a lamp and, thus, little or no improvement in efficiency of the UV light may be realized by altering its propagation. Furthermore, room/area decontamination systems are specifically designed to disperse light over a vast area and, thus, altering UV propagation from such systems may hinder such an objective. At the current time, use of HINS light in disinfection systems is in its infancy of development. No configurations are known which aid the propagation of HINS light to improve its disinfection efficacy in a room or for any other disinfection application other than what is used in conventional UV disinfection apparatuses.

Accordingly, it would be beneficial to develop germicidal lamp apparatuses having features and/or configurations of components which improve the propagation of germicidal light toward desired objects and/or regions of a room in order to improve disinfection efficiency of the apparatus. In addition, it would be beneficial to develop room/area decontamination systems which are more effective and more efficient than conventional room/area decontamination systems.

SUMMARY OF THE INVENTION

The following description of various embodiments of apparatuses is not to be construed in any way as limiting the subject matter of the appended claims.

Embodiments of apparatuses include a support structure comprising an upper base and a lower base vertically spaced from each other and first and second elongated germicidal lamps each with opposing ends respectively coupled to the upper and lower bases. The longitudinal axis of the first elongated germicidal lamp is at an acute angle greater than 0° relative to a region of the lower base between the first and second elongated germicidal lamps and the longitudinal axis of the second elongated germicidal lamp is at either a right angle or an obtuse angle relative to said region of the lower base.

Other embodiments of apparatuses include a plurality of germicidal lamps and a reflector adjacent the plurality of germicidal lamps, wherein the reflector comprises multiple sections each contoured to manipulate directionality of light emitted from a subset of the plurality of germicidal lamps. In addition, the apparatus is configured to move the reflector and/or collectively move the plurality of germicidal lamps during illumination of the plurality of germicidal lamps such that positions of each of the plurality of germicidal lamps relative to the multiple sections of the reflector is altered.

Yet other embodiments of apparatuses include a support structure comprising an upper base and a lower base vertically spaced from each other and a plurality of elongated germicidal lamps disposed between the upper and lower bases. In addition, such apparatuses include a reflector system common to the plurality of elongated germicidal lamps and disposed between the upper and lower bases, wherein the reflector system comprises a reflector with slanted peripheral edge.

BRIEF DESCRIPTION OF THE DRAWINGS

Other objects and advantages of the invention will become apparent upon reading the following detailed description and upon reference to the accompanying drawings in which.

Figure 1:
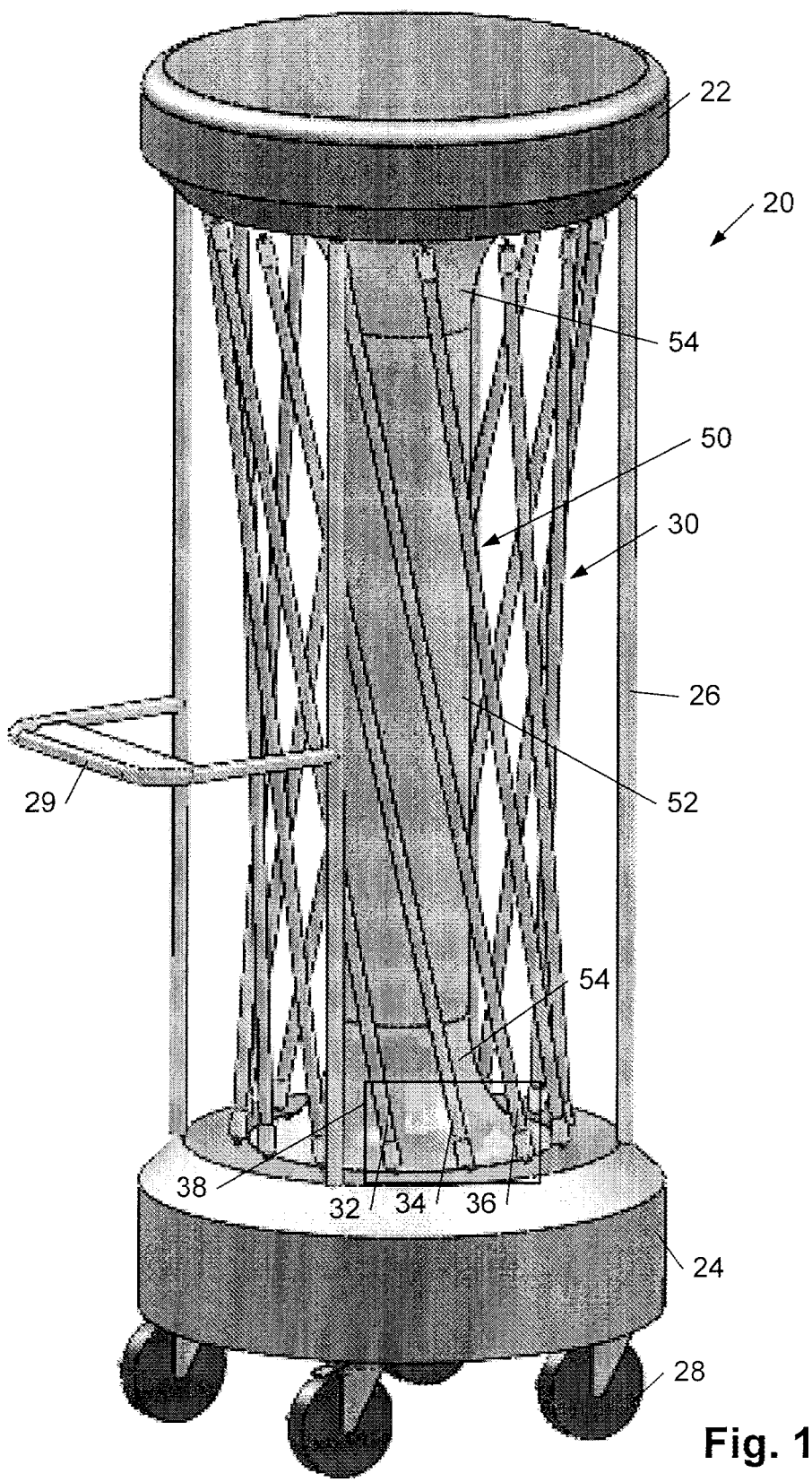
FIG. 1 illustrates an apparatus with slanted germicidal lamps and a reflector system common thereto.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 4:
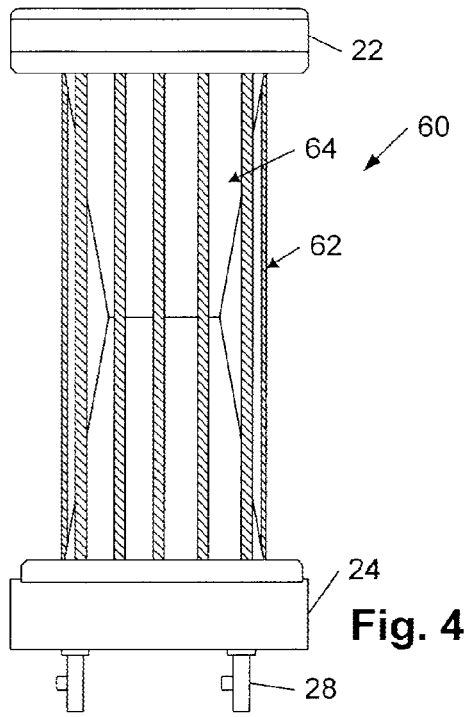
FIG. 4 illustrates a side view of an apparatus having a plurality of germicidal lamps disposed around an hour glass reflector.
Figure 6:
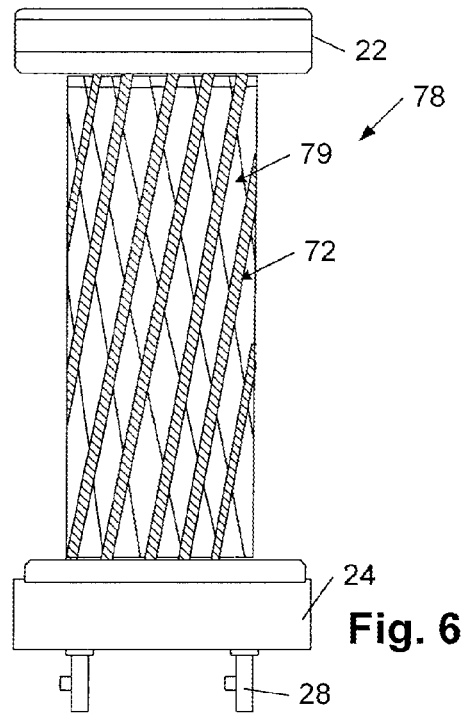
FIG. 6 illustrates yet another apparatus with a plurality of germicidal lamps disposed around a reflector having sections which are each contoured to manipulate directionality of light emitted from a subset of the plurality of germicidal lamps.
Figure 7:
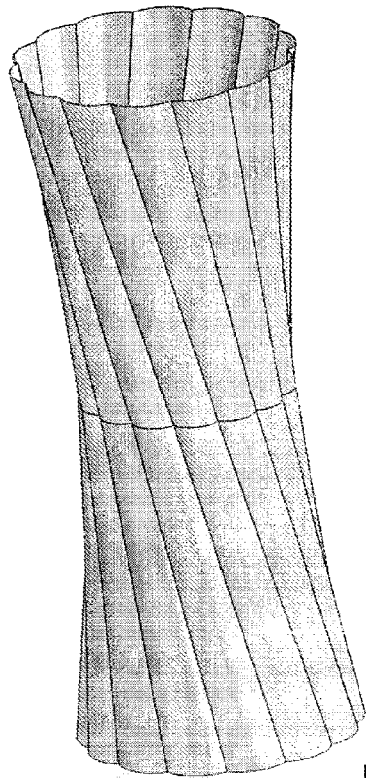
FIG. 7 illustrates an example reflector suitable for the apparatuses depicted in FIGS. 5 and 6 having convex sections.
Figure 8:
FIG. 8 illustrates an example reflector suitable for the apparatuses depicted in FIGS. 5 and 6 having concave sections.
Figure 5:
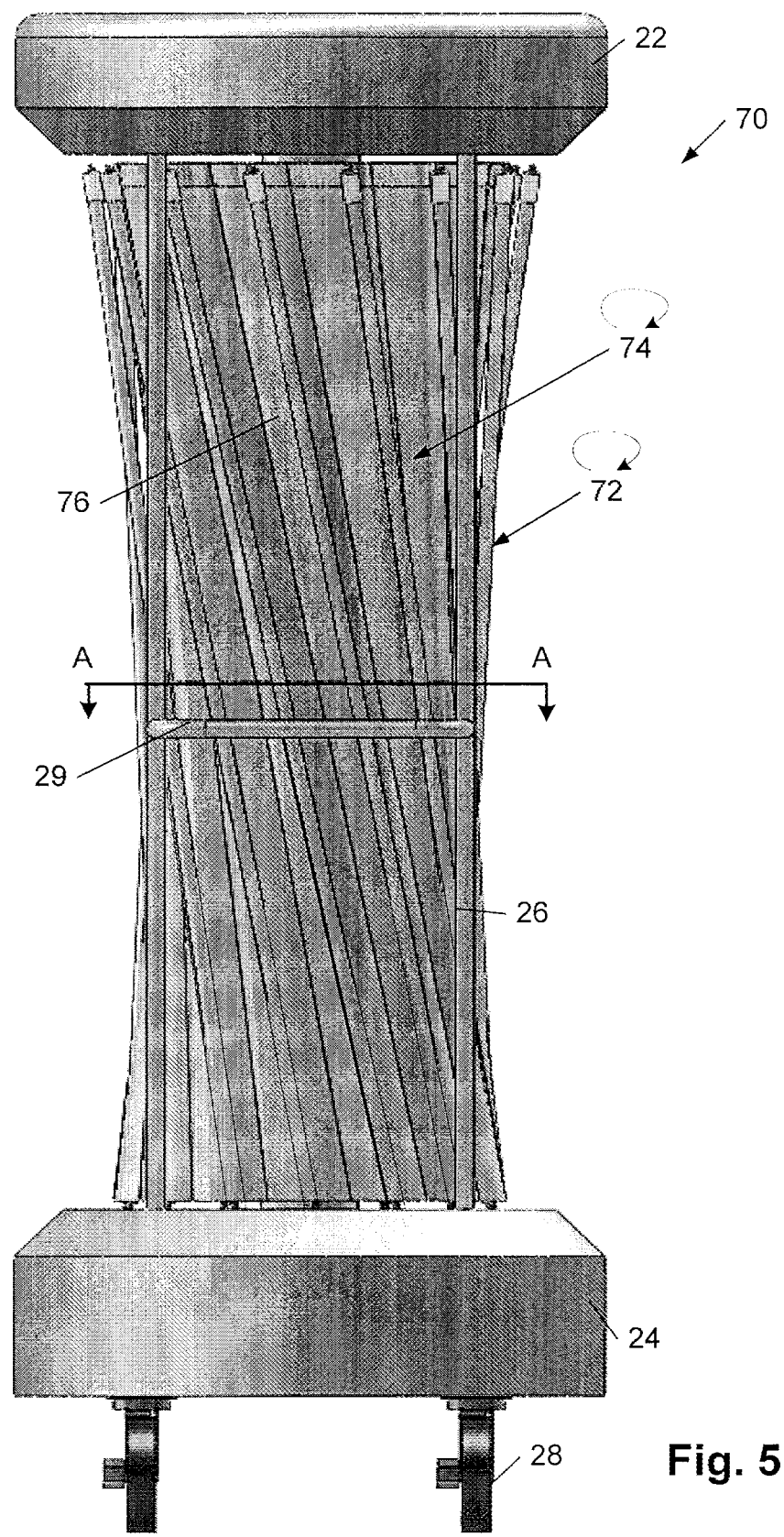
FIG. 5 illustrates a perspective view of another apparatus with a plurality of germicidal lamps disposed around a reflector having sections which are each contoured to manipulate directionality of light emitted from a subset of the plurality of germicidal lamps.
Figure 11:
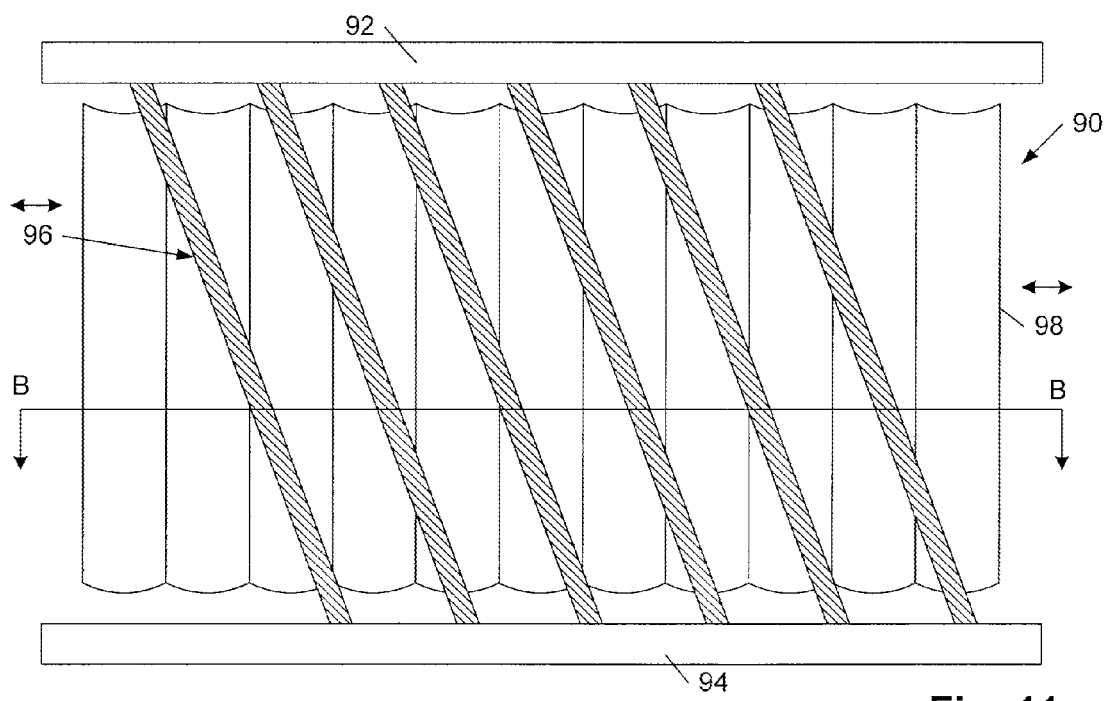
FIG. 11 illustrates an apparatus with a linear array of germicidal lamps arranged adjacent to a contoured reflector plate.

Turning to the drawings, examples of lamp and reflector arrangements for apparatuses having a plurality of germicidal lamps are shown. In particular, FIG. 1 shows apparatus 20 with a plurality of germicidal lamps 30 disposed between and slanted relative to surfaces of upper base 22 and lower base 24. In addition, FIG. 1 illustrates apparatus 20 with reflector system 50 disposed within the space encompassed by germicidal lamps 30. FIG. 4 similarly depicts apparatus 60 with a reflector system central to a plurality of germicidal lamps, but the configuration of the lamps and the reflector system differ from those depicted in FIG. 1. In particular, FIG. 4 shows germicidal lamps 62 vertically disposed between upper base 22 and lower base 24 and reflector system 64 including an hour glass shape. FIG. 5 illustrates yet another apparatus with a reflector system disposed within the space encompassed by a plurality of germicidal lamps. In particular, FIG. 5 depicts apparatus 70 with a plurality of germicidal lamps 72 disposed between and slanted relative to surfaces of upper base 22 and lower base 24. In addition, FIG. 5 depicts apparatus 70 with reflector system 74 having multiple panels each contoured to manipulate directionality of light emitted from a subset of the plurality of germicidal lamps. FIG. 6 illustrates apparatus 78 similar to apparatus 70 of FIG. 5 but with plurality of germicidal lamps 72 slanted in the opposite direction than the reflector panels of reflector system 79. FIGS. 7 and 8 illustrate different configurations for reflector systems 74 and 79 of FIGS. 5 and 6, specifically reflector systems respectively including convex and concave panels. FIG. 11 illustrates an alternative apparatus 90 with a linear array of slanted germicidal lamps 96 and reflector system 98 adjacent and common to the germicidal lamps 96.

It is noted that although the lamp and reflector configurations and arrangements disclosed herein are specifically described in reference to apparatuses having a plurality of germicidal lamps, any of such configurations and arrangements may be applied to an apparatus having a single germicidal lamp. Furthermore, although the lamp and reflector configurations and arrangements disclosed herein are described in reference to elongated cylindrical lamps, any of such configurations and arrangements may be applied to apparatuses having other configurations of lamps. As will be set forth in more detail below, the apparatuses and features described herein are not limited to the depictions in the drawings, including that the discharge lamps are not restricted to being slanted. Furthermore, it is noted that the drawings are not necessarily drawn to scale in that particular features may be drawn to a larger scale than other features to emphasize their characteristics.

Each of the apparatuses described herein includes a germicidal lamp. The term "germicidal lamp" as used herein refers to a light source designed to generate and emit germicidal light, i.e., light which is capable of deactivating or killing microorganisms, particularly disease carrying and/or disease producing microorganisms (a.k.a., germs). The term "kill," as used herein, means to cause the death of an organism. The term "deactivate," as used herein, means to render an organism unable to reproduce without killing. The germicidal lamps considered for the apparatuses described herein may be configured to generate any type of germicidal light, including ultraviolet light and high-intensity narrow-spectrum (HINS) light. In some embodiments, a germicidal lamp may generate additional ranges of light, particularly those which are not germicidal, but such capability will not deter from the reference of the lamps being germicidal.

In general, the germicidal lamps considered for the apparatuses described herein may be of any size and shape, depending on the design specifications of the apparatuses. In addition, the germicidal lamps considered for the apparatuses described herein may include those which generate continuous light and/or those which generate light in short durations, the latter of which are referred to herein as flashtubes or flashlamps. Flashtubes or flashlamps that are used to supply recurrent pulses of light are referred to herein as pulsed light sources. In any case, the apparatuses described herein are absent of optics for producing a laser from light emitted from a germicidal lamp and, accordingly, may be referred to herein as non-laser apparatuses in some embodiments. Alternatively stated, the apparatuses described herein are configured to propagate light emitted from a germicidal lamp in a non-laser fashion. As set forth in more detail below, some of the apparatuses described herein may be configured to expose areas and rooms as well as objects as a whole to germicidal light and, thus, are specifically configured to distribute light in a spacious manner rather than producing a narrow beam of limited diffraction as generated by lasers.

Examples of ultraviolet light lamps which may be considered for the apparatuses described herein include discharge lamps and light emitting diode (LED) solid state devices. HINS lamps are generally constructed of LEDs. A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the ultraviolet lamps which may be considered for the apparatuses described herein include gas-discharge lamps as well as surface-discharge lamps. Discharge lamps may be further characterized by the type of gas/es employed and the pressure at which they are operated. The discharge lamps which may be considered for the apparatuses described herein include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof.

A commonly used gas-discharge lamp used to produce continuous light is a mercury-vapor lamp, which may be considered for some of the apparatuses described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the apparatuses described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for some of the apparatuses described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the apparatuses described herein to include such lamps. Rather, the aforementioned descriptions and comparisons are merely provided to offer factors which one skilled in the art may contemplate when selecting a discharge lamp for an ultraviolet discharge lamp apparatus, particularly depending on the objective and application of the apparatus.

Turning to FIG. 1, apparatus 20 is shown with a plurality of germicidal lamps 30 disposed between upper base 22 and lower base 24. The term "base" as used herein refers to a part of a support structure of an apparatus onto or into which components of the apparatus are attached. Other features making up the support structure of apparatus 20 include support arms 26, wheels 28 and handle 29, all for transporting the apparatus, but they may be omitted depending on the design specifications of the apparatus. As shown in FIG. 1, upper base 22 and lower base 24 are vertically spaced from each other and provide electrical sockets to which the opposing ends of germicidal lamps 30 may be coupled. The placement and angle of the electrical sockets are such that germicidal lamps 30 are slanted with respect to the coupling surfaces of upper base 22 and lower base 24. In particular, the electrical sockets are arranged such that the longitudinal axis of each of germicidal lamps 30 is at an acute angle greater than 0° relative to a region of lower base 24 between one side of a given lamp and a neighboring lamp. In addition, the longitudinal axis of each of germicidal lamps 30 is at is at an obtuse angle relative to another region of lower base 24 between the opposing side of the lamp and a neighboring lamp. Moreover, the electrical sockets are arranged such that the longitudinal axis of each germicidal lamp is arranged at an obtuse angle and an acute angle relative to regions of upper base 22 on opposing sides of a lamp. In this manner, neighboring germicidal lamps 30 are slanted toward each other as is shown in FIG. 1.

In some embodiments, the electrical sockets on both upper base 22 and lower base 24 may be equally spaced and a circumference of a region demarcated by the electrical sockets on upper base 22 may be substantially equal to a circumference of a region demarcated by the electrical sockets on lower base 24. In such cases, the positions of germicidal lamps 30 (i.e., their longitudinal axes) are substantially uniform and parallel. In other embodiments, the electrical sockets on both upper base 22 and lower base 24 may not be equally spaced and/or a circumference of a region demarcated by the electrical sockets on upper base 22 may not be substantially equal to a circumference of a region demarcated by the electrical sockets on lower base 24. As a consequence, the positions of germicidal lamps 30 (i.e., their longitudinal axes) are not uniform or parallel. In such cases, however, subsets of neighboring lamps may be parallel to each other, depending on their relative arrangement.

Figure 2:
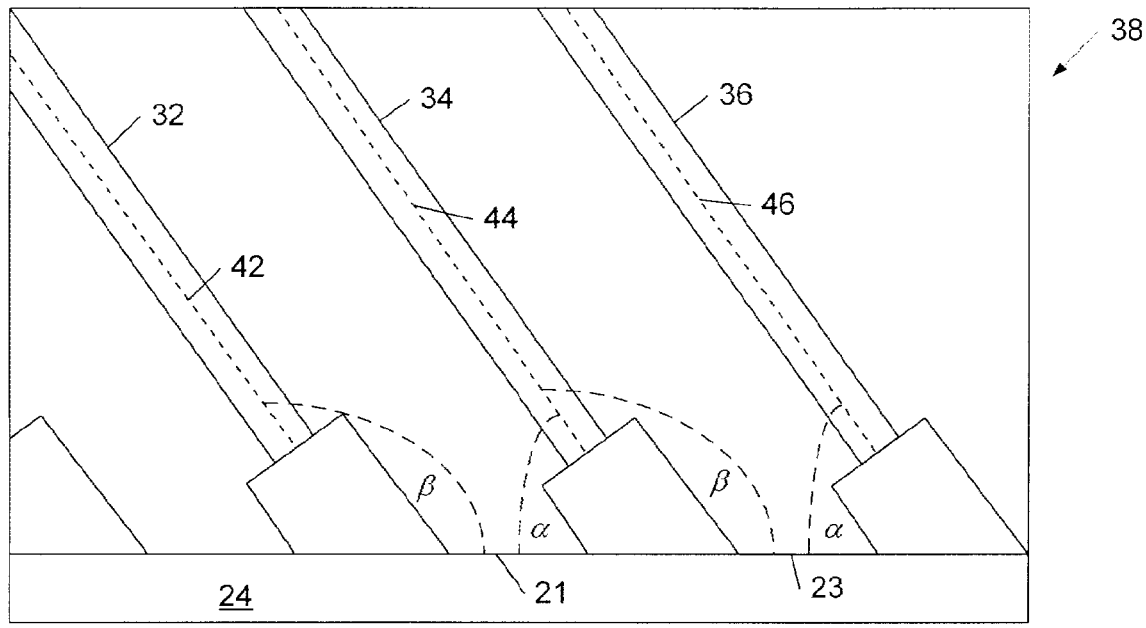
FIG. 2 is a magnified view of a portion of the apparatus depicted in FIG. 1.

A magnified view of portion 38 of apparatus 20 is shown in FIG. 2 detailing an example arrangement of neighboring germicidal lamps 32, 34 and 36 within apparatus 20. In particular, FIG. 2 illustrates neighboring germicidal lamps 32 and 34 arranged relative to region 21 of lower base 24, specifically a region of lower base 24 between the germicidal lamps 32 and 34. As shown, germicidal lamp 32 is arranged such that its longitudinal axis 42 is at obtuse angle $\beta$ relative to region 21 and germicidal lamp 34 is arranged such that its longitudinal axis 44 is at acute angle $\alpha$ relative to region 21. In such cases, acute angle $\alpha$ is greater than 0° as shown. In addition, germicidal lamp 34 is arranged such that its longitudinal axis 44 is at obtuse angle $\beta$ greater than 0° relative to region 23 of lower base 24 and germicidal lamp 36 is arranged such that its longitudinal axis 46 is at acute angle $\alpha$ relative to region 23. The values for acute angle $\alpha$ and obtuse angle $\beta$ for each lamp may generally depend on the design specifications of the apparatus. In some cases, each germicidal lamp of apparatus 20 may be arranged with the same acute angle and obtuse angle relative to regions of lower base 24 on opposing sides of the lamp and interposed between neighboring lamps. In other embodiments, the value of acute angle $\alpha$ and obtuse angle $\beta$ may be different for one or more lamps.

Figure 3:
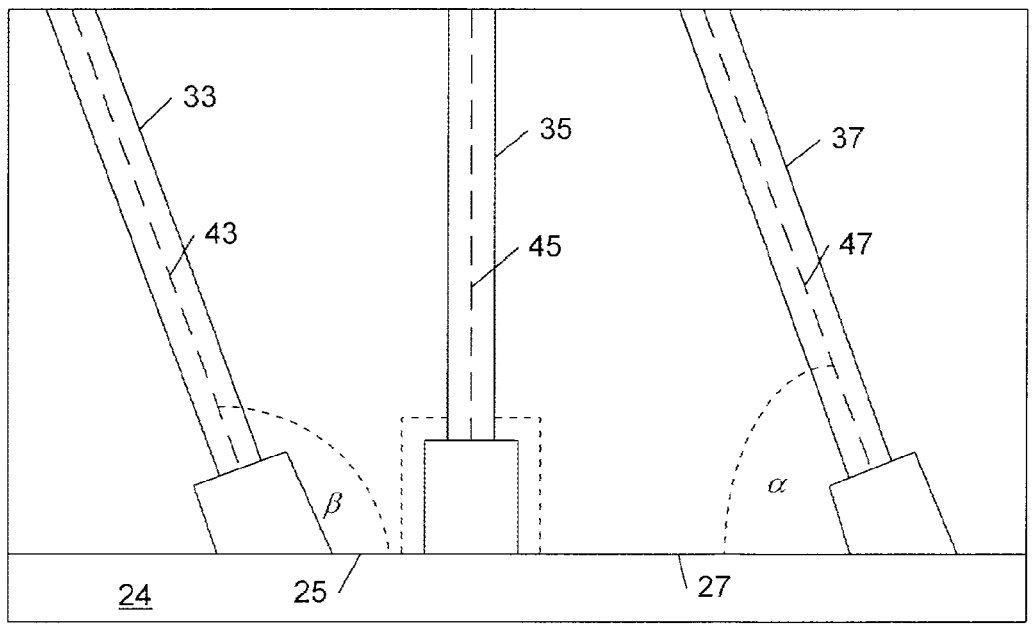
FIG. 3 illustrates an alternative arrangement of germicidal lamps for the apparatus depicted in FIG. 1 in the magnified viewpoint of FIG. 2.

In some cases, not all the plurality of germicidal lamps 30 of apparatus 20 may be arranged with opposing sides respectively arranged an acute angle and an obtuse angle relative to regions of lower base 24 that are interposed between neighboring lamps. In particular, one or more of germicidal lamps 30 may be arranged upright such that their longitudinal axis is at a right angle at least on either side of the lamp with respect to regions of lower base 24 interposed between the lamp and neighboring lamps. FIG. 4 illustrates an example of an apparatus with all germicidal lamps arranged upright as described in more detail below. FIG. 3 illustrates an example of an embodiment which has upright germicidal lamp 35 interposed and neighboring slanted germicidal lamps 33 and 37 as an alternative to the configuration of germicidal lamps 32, 34 and 36 illustrated in FIG. 2. In particular, FIG. 3 illustrates germicidal lamp 33 arranged such that its longitudinal axis 43 is at obtuse angle $\beta$ relative to region 25 of lower base 24 and germicidal lamp 35 is arranged such that its longitudinal axis 45 is at a right angle relative to region 25. In addition, FIG. 3 illustrates germicidal lamp 37 arranged such that its longitudinal axis 47 is at acute angle $\alpha$ relative to region 27 of lower base 24 and germicidal lamp 38 is arranged such that its longitudinal axis 45 is at a right angle relative to region 27. As with the configuration noted in FIG. 2, the values for acute angle $\alpha$ and obtuse angle $\beta$ for lamps 33 and 37 may generally depend on the design specifications of the apparatus. It is noted that the apparatuses considered herein having a combination of vertical and slanted lamps are not restricted to the alternating sequence depicted in FIG. 3. In particular, the apparatuses described herein may include any number of vertical and slanted lamps arranged in any patterned or non-patterned sequence.

Slanted configurations of one or more germicidal lamps 30 may be advantageous for a number of reasons. For one, such a configuration will reduce the shadowing effect around support bars 26 of the apparatus. Furthermore, slanted configurations of germicidal lamps may be advantageous for some of the reflector configurations described in more detail below, particularly in reference to FIGS. 7 and 8. Given such advantages, however, it is noted that the apparatuses described herein are not necessarily restricted to having slanted germicidal lamps. In particular, the apparatuses described herein may include germicidal lamps arranged at right angles relative to regions of lower base 24 on opposing sides of the lamp and interposed between neighboring lamps. Furthermore, the germicidal lamps of the apparatuses considered herein need not be restricted to a circular arrangement around a common reference axis of the apparatus such as shown in FIG. 1. In particular, the germicidal lamps may be arranged in any configuration around a common reference axis of an apparatus, such as in a square or rectangular arrangement. Furthermore, the distance of some or all of the germicidal lamps need not be the same from a common reference axis of an apparatus. In yet other case, germicidal lamps may not be arranged around a common reference axis of an apparatus.

It is further noted that regardless of whether an apparatus includes vertical and/or slanted lamps as referenced above, the lamps may be angled inward toward a common reference axis of the apparatus (e.g., a central axis of the apparatus) or may be parallel to such axis. For example, in embodiments in which all of the same ends of germicidal lamps 30 (i.e., the ends coupled to upper base 22 or the ends coupled to lower base 24) are angled inward toward a common reference axis of apparatus 20, the arrangement of the germicidal lamps 30 may generally be conical. In yet other embodiments, different ends of germicidal lamps 30 may be angled inward toward the common reference axis. In other cases, some or all of the germicidal lamps 30 may be parallel to the common reference axis. In any case, it is noted that the arrangement of lamps being angled or parallel toward a common reference axis of an apparatus does not affect whether the lamps are arranged at an acute, obtuse or a right angle relative to a neighboring lamp.

Furthermore, although germicidal lamps 30 are shown coupled to upper base 22 and lower base 24 in FIG. 1, the lamps are not necessarily so restricted. In particular, apparatus 20 may, in some embodiments, include intermediary bases between upper base 22 and lower base 24 for coupling ends of germicidal lamps 30. In such cases, germicidal lamps 30 may be spaced apart from upper base 22 and/or lower base 24 and, in some embodiments, the ends of germicidal lamps 30 may be coupled near the opposing ends of middle section 52 of reflector 50. In the latter of such cases, apparatus 20 may, in some embodiments, include additional germicidal lamps adjacent to upper section 54 and/or lower section 56 of reflector 50.

Regardless of the configuration of germicidal lamps in the apparatuses considered herein, the apparatuses may, in some embodiments, include a reflector system common to the germicidal lamps. In particular, the apparatuses may include a centralized reflector system having reflectors which reflect light emitted from one or more of the germicidal lamps. For example, apparatus 20 shown in FIG. 1 includes reflector system 50 interior to the arrangement of germicidal lamps 30. In general, the material of the reflectors described herein may be any found suitable for the desired redirection of light. An exemplary reflector material found suitable for many of the apparatus configurations described herein is 4300UP Miro-UV available from ALANOD Aluminium-Veredlung GmbH & Co. KG. Another exemplary reflector material found suitable for many of the apparatus configurations described herein is GORE® DRP® Diffuse Reflector Material available from W. L. Gore & Associates, Inc. Yet another reflector material may include a substrate covered with expanded polytetrafluoroetheylene (ePTFE), which has shown to have greater reflectivity than aluminum. Other reflector materials may be additionally or alternatively used, depending on the design specifications of the reflection system.

In particular configurations, the reflector systems considered herein may be specifically configured to concentrate light toward a region between approximately 2 feet and approximately 4 feet from a floor of a room in which an apparatus is arranged. In general, the region between approximately 2 feet and approximately 4 feet from a floor of a room is considered a "high touch" region of a room since objects of frequent use are generally placed in such a region. Examples of objects typically found in a high touch zone of a room include but are not limited to desktops, keyboards, telephones, chairs, door and cabinet handles, light switches and sinks Examples of objects in high touch zones of hospital rooms additionally or alternatively include beds, bedside tables, tray tables and intravenous stands. Due to such a region being considered a high touch zone, it is generally considered the area of highest probability to come in contact with germs and some studies indicate that the high touch zone may be the area having the highest concentration of germs. For such reasons, it may be advantageous to direct at least some ultraviolet light to a region which is between approximately 2 feet and approximately 4 feet from a floor of a room.

As shown in FIG. 1, reflector system 50 includes middle section 52, upper section 54 and lower section 56. As illustrated, upper and lower sections 54 and 56 are configured to direct light emitted from germicidal lamps 30 in substantially downward and upward directions, respectively. In addition, middle section 52 is configured to direct light emitted from germicidal lamps 30 sideways from the lamp. Given that apparatus 20 is generally about 5 feet tall, the configurations of middle section 52, upper section 54 and lower section 56 may concentrate light propagating from apparatus 20 toward a region between approximately 2 feet and approximately 4 feet from a floor of a room in which apparatus 20 is arranged.

In general, the size, shape and configuration of sections 52, 54 and 56 may vary among apparatuses. For instance, middle section 52 may include any shape and, thus, middle section 52 is not restricted to being cylindrical. Similarly, upper section 54 and lower section 56 may include any shape and, thus, are not restricted to being conical. In addition, the peripheries of upper section 54 and lower section 56 may be stepped or straight edged and, thus, are not restricted to the smooth curvatures depicted in FIG. 1. Furthermore, upper section 54 and lower section 56 need not be symmetrical. In some cases, the configurations of upper section 54 and lower section 56 may be reversed such that light will be directed upward and downward, respectively. In yet other embodiments, upper section 54 and/or lower section 56 may be omitted from reflector system 50.

Furthermore, the length of middle section 52 may vary depending on the design specifications (e.g., size) of the apparatus. In some embodiments, middle section 52 may be omitted from reflector system 50. In such cases, upper and lower sections 54 and 56 of reflector system 50 may be joined, forming an hour glass shaped reflector common to germicidal lamps 30. An example of an apparatus with an hour glass shaped reflector is shown in FIG. 4. In particular, FIG. 4 illustrates apparatus 60 including hour glass reflector 64 central to plurality of germicidal lamps 62. It is noted that features depicted in FIG. 4 with the same configurations as described in reference to FIG. 1 (e.g., upper base 22 and lower base 24) are denoted with the same reference numbers and the descriptions of such features are not reiterated for the sake of brevity. Support arms and a handle for the support structure have been omitted from the figure to simplify its illustration, but such components may be part of apparatus 60.

In general, the size and shape of hour glass reflector 64 may vary among apparatuses depending on their design specifications. In particular, the length and width of hour glass reflector 64 may be selected based on a size of an apparatus. In addition, the shape and gradient of the contours between the widest and narrowest portion of hour glass reflector 64 may vary among apparatuses. In some cases, the areal dimensions of the top and bottom sections of hour glass reflector 64 (segregated by the narrowest portion of the hour glass) may be substantially equal as depicted in FIG. 4. In other cases, however, the length and/or overall area of the top and bottom sections of hour glass reflector 64 may not be equal. As shown in FIG. 4, germicidal lamps 62 may be arranged upright between upper base 22 and lower base 24 such that their longitudinal axes are at right angles at least with respect to regions of upper base 22 and lower base 24 between the lamp and the neighboring lamps (i.e., neighboring lamps are not slanted toward each other). The hour glass configuration of reflector 64, however, is not mutually exclusive to upright lamps and, thus, in some embodiments, one or more of germicidal lamps 62 may be slanted toward their neighboring lamp as described above for germicidal lamps 30.

Another configuration of a reflector system which may be considered for the apparatuses described herein includes a reflector having multiple sections or panels each contoured to manipulate directionality of light emitted from a subset of germicidal lamps. An example of an apparatus with such a reflector system is depicted in FIG. 5. In particular, FIG. 5 depicts apparatus 70 including sectioned reflector 74 central to plurality of germicidal lamps 72. It is noted that features depicted in FIG. 5 with the same configurations as described in reference to FIG. 1 (e.g., upper base 22 and lower base 24) are denoted with the same reference numbers and the descriptions of such features are not reiterated for the sake of brevity. As shown in FIG. 5, reflector 74 includes sections 76 each aligned with a single respective germicidal lamp. In particular, reflector 74 includes the same number of sections 76 as the number of germicidal lamps 72 and reflector 74 is arranged such that each germicidal lamp is aligned with a central portion of a respective section 76. Such a configuration may be particularly advantageous for manipulating the directionality of light emitted from each germicidal lamp. Other configurations of reflectors, however, may be considered. For example, the number of sections 76 of reflector 74 may, in some cases, be more or less than the number of germicidal lamps 72. In addition or alternatively, reflector 74 need not be in an hour glass shape. In particular, reflector 74 may alternatively have substantially vertical sidewalls or sidewalls which bow out. In addition or alternatively, germicidal lamps 72 need not be slanted relative to each other. In particular, one or more of germicidal lamps 72 may be arranged at a right angle relative to a space between the lamp and a neighboring lamp.

Furthermore, germicidal lamps 72 need not be aligned with a central portion of one of sections 76 as is depicted in FIG. 5. In particular, germicidal lamps 72 may be alternatively aligned with off-center portions of sections 76. In some embodiments, germicidal lamps 72 may be slanted at a different angle than sections 76. In other cases, germicidal lamps 72 may be slanted in the opposite direction than sections 76. In yet other embodiments, germicidal lamps 72 may not be slanted relative to the regions of upper base 22 and lower base 24 between neighboring lamps. In particular, germicidal lamps 72 may, in some cases, be arranged upright to such regions of upper base 22 and lower base 24. An example of an apparatus with germicidal lamps slanted in an opposite direction than sections of a reflector is depicted in FIG. 6. In particular, FIG. 6 illustrates apparatus 78 including sectioned reflector 79 central to plurality of germicidal lamps 72. It is noted that features depicted in FIG. 6 with the same configurations as described in reference to FIG. 1 (e.g., discharge lamps 72, upper base 22, and lower base 24) are denoted with the same reference numbers and the descriptions of such features are not reiterated for the sake of brevity. Support arms and a handle for the support structure have been omitted from the figure to simplify its illustration, but such components may be part of apparatus 78. As with apparatus in FIG. 5, apparatus 78 in FIG. 6 is not limited to having the same number of reflector sections as those of discharge lamps 72. In addition or alternatively, reflector 79 need not be in an hour glass shape.

As noted above, each of sections 76 of apparatus 70 are contoured to manipulate directionality of light emitted from a subset of germicidal lamps. In general, the contours of sections 76 may include any shape, size and configuration to achieve such an objective. In some cases, sections 76 may be contoured in the same manner, but in other embodiments, the contours of one or more sections 76 may differ. The same generalities are also applicable to sections of reflector 79 described in reference to FIG. 6. Examples of contours which may be used for reflectors 76 and 79 in respective apparatuses 70 and 78 include convex curvatures and concave curvatures. An example of a reflector having convex sections is illustrated in FIG. 7 and an example of a reflector having concave sections is illustrated in FIG. 8. In general, a reflector having convex sections may be advantageous for increasing the intensity of light propagating from an apparatus relative to what may be generated by the germicidal lamp alone, but diffusing such light in a spacious manner in a given area. In contrast, a reflector having concave sections may be advantageous for generating even greater intensity of light propagating from an apparatus, but the light emitted from the concave sections will be more focused and, thus, not distributed as spaciously as done by a convex section. In some cases, a reflector may include a combination of convex and concave sections to offer a both types of light distribution from an apparatus. In particular embodiments, the convex and concave sections may alternate in sequence in a system in an effort to try to mitigate the lack of light distribution from the concave sections. Other arrangements of the convex and concave sections may be considered as well.

In some embodiments, an apparatus may be configured to change the configuration of a reflector's multiple sections, particularly their contours. For example, an apparatus may be configured to alter the configuration of a reflector's multiple sections between convex and concave curvatures. For instance, a reflector may be constructed of a pliable material sufficient to allow midlines of the sections to be pulled out or pushed in to affect such curvature change. In such cases, the change in curvature may, in some embodiments, be affected by pushing or pulling sections manually one at a time or the apparatus may include a means for affecting pulling and pushing movements of the sections of any number of the sections at once. An example of a means for affecting pulling and pushing movements of the sections may include an assembly of rods each attached to a section of the reflector along the interior of the reflector and one or more mechanical levers attached to the assembly of rods. In yet other embodiments, a means for affecting pushing and pulling of sections may be a blower and vacuum system arranged in the interior of the reflector. In particular, convex sections may be changed to concave sections by blowing a gas into the interior of the reflector and, conversely, concave sections may be changed to convex sections by creating a vacuum in the interior of the reflector. In such cases, the application of gas or vacuum may be individualized to each section or a subset of the sections, or alternatively may be distributed to all sections at once. Other means for affecting pushing and pulling of sections of a reflector to affect curvature change may be considered as well.

In any case, in embodiments in which an apparatus includes a means for affecting pulling and pushing movements of the sections (e.g., rods attached to the sections or a blower and vacuum system), the apparatus may, in some embodiments, may include another means for automating activation of the means. For instance, the apparatus may include processor executable program instructions for activating the means for affecting pulling and pushing movements of the sections in response to a directive to do so or upon receiving information and/or measurements related to the operation of the apparatus and/or characteristics of the room in which the apparatus is arranged. U.S. patent application Ser. No. 13/706,926 to Mark Stibich filed Dec. 6, 2012, entitled "Systems which Determine Operating Parameters and Disinfection Schedules for Germicidal Devices" describes disinfection systems having processor executable program instructions for receiving data regarding the characteristics of a room in which a disinfection source is arranged and determining, based on the data, one or more individual operating parameters for the disinfection source. It is noted that the teachings in U.S. patent application Ser. No. 13/706, 926 regarding receipt and determination of room characteristics and/or information relative to the disinfection efficiency of the apparatus are applicable and may be beneficial for a means for affecting pulling and pushing movements of reflector sections. U.S. patent application Ser. No. 13/706,926 is incorporated by reference as if fully set forth herein.

Figure 9:
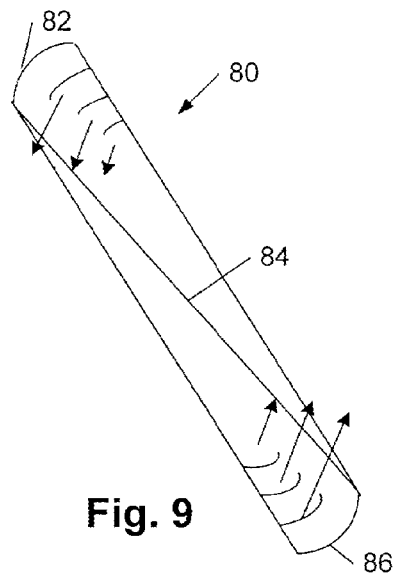
FIG. 9 illustrates an example of a reflector panel with a concave curvature having opposing ends twisted in opposite directions at angles less than or equal to approximately 90 degrees relative to a midsection of the concave curvature.

In any case, the configuration (i.e., the depth, relative position of sidewalls, etc.) of concave sections of a reflector may, in some embodiments, be substantially uniform from one end to the other. In other cases, however, ends of concave sections may differ in alignment. For example, in some cases, a reflector may have a concave curvature having opposing ends twisted in opposite directions at angles less than or equal to approximately 90 degrees relative to a midsection of the concave curvature. An example of a concave section with such a configuration is illustrated in FIG. 9. In particular, FIG. 9 illustrates concave section 80 of a reflector having opposing ends 82 and 86 twisted in opposite directions at angles less than or equal to approximately 90 degrees relative to midsection 84 of the concave curvature. Such a configuration propagates light from opposing ends 82 and 86 downward and upward, respectively. In this manner, light may be focused to a vertical section of a room which is smaller in height than the length of the reflector. For example, such a configuration may be advantageous for concentrating light toward a region between approximately 2 feet and approximately 4 feet from a floor of a room in which an apparatus is arranged. In other cases, the direction opposing ends 82 and 86 are twisted may be reversed. In such embodiments, light from emitted from opposing ends 82 and 86 may be directed upward and downward, respectively.

Returning back to FIG. 5, regardless of the contour of sections 76, apparatus 70 may, in some cases, be configured to move reflector 74 and/or collectively move plurality of germicidal lamps 72 during illumination of the lamps such that position of each of the plurality of germicidal lamps relative to multiple sections 76 is altered. In particular, movement of reflector 74 and/or the collective movement of germicidal lamps 72 will change the directionality of the light emitted from respective sections 76, in effect distributing the light more uniformly throughout a room in which apparatus 70 is arranged. For the configuration of apparatus 70 in which germicidal lamps 72 are disposed about a common reference axis of the apparatus, the movement of reflector 74 and/or the collective movement of germicidal lamps 72 may be about the common reference axis. In particular, apparatus 70 may be configured to oscillate or rotate reflector 74 and/or germicidal lamps 72 at least partially while germicidal lamps 72 are illuminated. The direction of movement may be clockwise, counterclockwise, or a combination thereof. In embodiments in which both are moved, the direction of movement of reflector 74 and germicidal lamps 72 may be the same in some embodiments, but at different times or speeds. Alternatively, the direction of movement of reflector 74 and germicidal lamps 72 may be different.

It is noted that movement of reflector 74 and/or germicidal lamps 72 is not restricted to when germicidal lamps 72 are illuminated. In particular, in embodiments in which germicidal lamps 72 include pulsed light sources, reflector 74 and/or germicidal lamps 72 may move between pulses of light in addition to moving during the pulses of light. Furthermore, movement of reflector 74 and/or germicidal lamps 72 may occur for entire duration of a disinfection process or may occur for a duration less than an entire disinfection process for apparatus 70. Moreover, the movement of reflector 74 and/or germicidal lamps 72 may be continuous or periodic during a disinfection process for apparatus 70.

Figure 10:
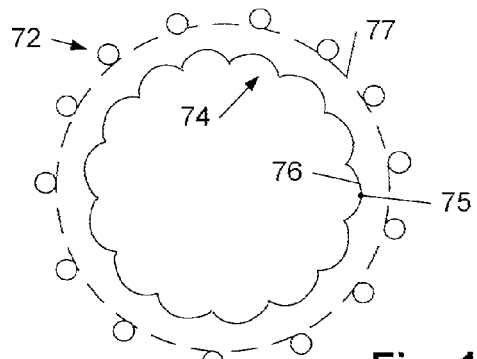
FIG. 10 illustrates a cross-sectional view of the apparatus depicted in FIG. 5 taken along axis AA.

As noted above, the movement of reflector 74 and/or germicidal lamps 72 is about a common reference axis of apparatus 70 and, thus, the overall areal space between reflector 74 and germicidal lamps 72 is maintained, but the position of each of the plurality of germicidal lamps relative to multiple sections 76 is altered. Alternatively stated, reflector 74 and/or germicidal lamps 72 are moved sideways at a set distance from the common reference axis of apparatus 60 and, thus, are not moved toward or away from each other. Another manner to describe such movement is that the distance between a given point on one of the multiple sections 76 to a virtual line which is tangential to surfaces of germicidal lamps 72 facing reflector 74 is unchanged. Such a description is depicted in FIG. 10, which is a cross-sectional view of apparatus 70 taken along axis AA. In particular, FIG. 10 illustrates point 75 on one of multiple sections 76 and further virtual line 77 tangential to surfaces of germicidal lamps 72 facing reflector 74. When either reflector 74 and/or germicidal lamps 72 are moved, the distance between point 75 and virtual line 77 is unchanged.

Although the lamp and reflector arrangements described above are with respect to apparatuses having a circumferential arrangement of lamps around a centralized reflector, the core ideas of the lamp and reflector arrangements are not necessarily so limited to such applications. In particular, any of the lamp and reflector arrangements described above may be applied to apparatuses having a non-circumferential arrangement of lamps. An example of such a system is depicted in FIG. 11. In particular, FIG. 11 shows apparatus 90 including linear array of germicidal lamps 96 disposed between upper base 92 and lower base 94 and adjacent reflector plate 98. As shown, linear array of germicidal lamps 96 may be slanted relative to areas of upper base 92 and lower base 94 between neighboring lamps such as specifically described above for germicidal lamps 30 in reference to FIG. 1. Similar to the embodiments described above in reference to FIGS. 1 and 4-6, germicidal lamps 96 may be slanted at a different angle than depicted in FIG. 11, in an opposite direction than depicted in FIG. 11, or may be arranged upright relative to areas of upper base 92 and lower base 94 between neighboring lamps.

As further shown in FIG. 11, reflector 98 may include sections contoured to manipulate directionality of light emitted from a subset of germicidal lamps 96. In particular, reflector 98 is shown to have sections with convex curvatures. In alternative embodiments, reflector 98 may include sections with concave curvatures. In either case, the section panels of reflector 98 may be slanted in some embodiments. In cases of sections having concave curvature, the section may, in some embodiments, include the configuration described for reflector panel 80 having opposing ends twisted in opposite directions at angles less than or equal to approximately 90 degrees relative to a midsection of the concave curvature. In yet other embodiments, the sections of reflector 98 may not be slanted as shown in FIG. 10 or reflector 98 may not have sections (i.e., reflector 98 may have a substantially flat plate surface). In any of such cases, reflector 98 may, in some cases, include a section approximate upper base 92 which is contoured to direct light emitted from germicidal lamps 96 in a substantially downward or upward direction such as described above for upper section 54 of reflector 50 in reference to FIG. 1. In addition or alternatively, reflector 98 may, in some cases, include a section approximate lower base 94 which is contoured to direct light emitted from germicidal lamps 96 in a substantially upward or downward direction such as described above for lower section 56 of reflector 50 in reference to FIG. 1.

Figure 12:
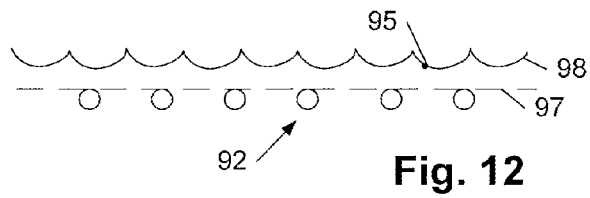
FIG. 12 illustrates a cross-sectional view of the apparatus depicted in FIG. 11 taken along axis BB.

Regardless of the configuration of reflector 98 and germicidal lamps 96, apparatus 90 may, in some cases, be configured to move reflector 98 and/or collectively move plurality of germicidal lamps 96 during illumination of the lamps such that position of each of the plurality of germicidal lamps relative to multiple sections 98 is altered as similarly described for reflector 74 and germicidal lamps 72 in reference to FIG. 5. In contrast to the rotational movement described in reference to FIG. 5, however, apparatus 90 may be configured to traverse reflector 98 and/or the collective movement of germicidal lamps 96 sideways for their movement. Such sideways movement alters the position of each of the plurality of germicidal lamps 96 relative to the multiple sections of reflector 98, but the overall areal space between reflector 98 and germicidal lamps 96 is maintained. Alternatively stated, reflector 98 and/or germicidal lamps 92 are moved sideways at a set distance from each other and are not moved toward or away from each other. Another manner to describe such movement is that the distance between a given point on one of the multiple sections of reflector 98 to a virtual line which is tangential to surfaces of germicidal lamps 96 facing reflector 98 is unchanged. In reference to such a description, FIG. 12 depicts a cross-sectional view of apparatus 90 taken along axis BB denoting point 95 on one of the multiple sections of reflector 98 and further virtual line 97 tangential to surfaces of germicidal lamps 96 facing reflector 98.

In overview of the reflector arrangements described herein, it is noted that a commonality among the arrangements is that the reflector systems include a slanted peripheral edge. In particular, reflector system 50 in FIG. 1 includes upper section 54 and lower section 56 each with a slanted peripheral edge. In addition, the hour glass shape of reflector 64 in FIG. 4 includes slanted peripheral edges. Moreover, the reflectors described in reference to FIGS. 5-12 having convex and/or concave curvatures include slanted peripheral edges. As such, it is set forth that apparatuses are set forth which include a support structure comprising an upper base and a lower base vertically spaced from each other, a plurality of elongated germicidal lamps disposed between the upper and lower bases, and a reflector system common to the plurality of elongated germicidal lamps and disposed between the upper and lower bases, wherein the reflector system comprises a reflector with slanted peripheral edge.

It will be appreciated to those skilled in the art having the benefit of this disclosure that this invention is believed to provide lamp and reflector arrangements for germicidal lamp systems and apparatuses, particularly those with a plurality of germicidal lamps. Further modifications and alternative embodiments of various aspects of the invention will be apparent to those skilled in the art in view of this description. For example, although the aforementioned discussions give specific use and configuration for area/room disinfection processes, the systems and apparatuses described herein are not so limited and may be used to disinfect or sterilize items in any type of environment or area, including those in a closed chamber. Furthermore, the lamp and reflector arrangements may be used in other applications which utilize ultraviolet light, such as for example polymer curing and medical procedures. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An apparatus, comprising:
    a support structure comprising an upper base and a lower base vertically spaced from each other; and
    first and second elongated germicidal lamps each with opposing ends respectively coupled to the upper and lower bases, wherein:
        a longitudinal axis of the first elongated germicidal lamp is at an acute angle greater than 0° relative to a region of the lower base between the first and second elongated germicidal lamps; and
        a longitudinal axis of the second elongated germicidal lamp is at either a right angle or an obtuse angle relative to said region of the lower base.

2. The apparatus of claim 1, wherein the longitudinal axes of the first and second elongated germicidal lamps are parallel to each other.

3. The apparatus of claim 1, wherein the longitudinal axes of the first and second elongated germicidal lamps are not parallel to each other.

4. The apparatus of claim 1, wherein the first and second elongated germicidal lamps neighbor each other among arrangement with additional elongated germicidal lamps of the apparatus.

5. The apparatus of claim 1, comprising additional elongated germicidal lamps, wherein the first and second elongated germicidal lamps and the additional elongated germicidal lamps are arranged about a common reference axis of the support structure.

6. The apparatus of claim 1, further comprising a reflector system spaced adjacent to one of the first and second elongated germicidal lamps, wherein the reflector system comprises at least one of:
 a section proximate the upper base of the apparatus which is contoured to direct light emitted from the adjacent elongated germicidal lamp in substantially downward direction; and
 a section proximate the lower base of the apparatus which is contoured to direct light emitted from the adjacent elongated germicidal lamp in substantially upward direction.

7. The apparatus of claim 1, further comprising a reflector spaced adjacent to one of the first and second elongated germicidal lamps, wherein the reflector comprises a concave curvature having opposing ends twisted in opposite directions at angles less than or equal to approximately 90 degrees relative to a midsection of the concave curvature.

8. An apparatus, comprising:
 a plurality of germicidal lamps; and
 a reflector adjacent the plurality of germicidal lamps, wherein the reflector comprises multiple sections each contoured to manipulate directionality of light emitted from a subset of the plurality of germicidal lamps, and wherein the apparatus is configured to automate movement of the reflector and/or collect movement of the plurality of germicidal lamps during illumination of the plurality of germicidal lamps such that positions of each of the plurality of germicidal lamps relative to the multiple sections of the reflector is altered.

9. The apparatus of claim 8, wherein the apparatus is configured to automate movement of the reflector and/or collect movement of the plurality of germicidal lamps during illumination of the plurality of germicidal lamps such that a distance between a given point on one of the multiple sections to a virtual line which is tangential to surfaces of the plurality of germicidal lamps facing the reflector is unchanged.

10. The apparatus of claim 8, wherein at least one of the multiple sections comprises a convex curvature.

11. The apparatus of claim 8, wherein at least one of the multiple sections comprises a concave curvature.

12. The apparatus of claim 8, wherein the plurality of germicidal lamps is arranged about a vertical reference axis, and wherein the reflector is concentric with the vertical reference axis.

13. The apparatus of claim 8, wherein the plurality of germicidal lamps is a linear array of germicidal lamps, and wherein the apparatus is configured to automate movement of the reflector in parallel with the plurality of germicidal lamps and/or is configured to automate collective movement of the plurality of germicidal lamps in parallel with the reflector.

14. The apparatus of claim 8, wherein the reflector is configured such that contours of the multiple sections may be altered.

15. The apparatus of claim 8, wherein the multiple sections of the reflector are panels each contoured to manipulate directionality of light emitted from a different subset of the plurality of germicidal lamps.

16. An apparatus for disinfecting a room, comprising:
 a support structure comprising an upper base and a lower base vertically spaced from each other;
 a plurality of elongated germicidal lamps each with opposing ends respectively coupled to the upper and lower bases; and
 a reflector system common to the plurality of elongated germicidal lamps and disposed between the upper and lower bases, wherein the reflector system comprises a reflector with a peripheral edge slanted relative to a horizontal plane of the apparatus.

17. The apparatus of claim 16, wherein the plurality of elongated germicidal lamps is arranged about a vertical reference axis extending through the support structure, and wherein the reflector comprises a reflector central to the plurality of elongated germicidal lamps.

18. The apparatus of claim 17, wherein the reflector comprise a conical reflector disposed in proximity to the upper or lower base.

19. The apparatus of claim 17, wherein the reflector comprises an hour glass shape.

20. The apparatus of claim 16, wherein the reflector is one of a plurality of reflector panels of the reflector system arranged at a slant relative to a horizontal plane of the apparatus.

21. The apparatus of claim 20, wherein one or more of the reflector panels are convex panels.

22. The apparatus of claim 20, wherein one or more of the reflector panels are concave panels.

23. The apparatus of claim 22, wherein at least one of the concave panels has opposing ends respectively twisted in opposite directions at angles of approximately 90 degrees or less relative to its midsection.

24. The apparatus of claim 20, wherein at least one of the plurality of elongated germicidal lamps is slanted relative to a horizontal plane of the apparatus.

25. The apparatus of claim 24, wherein the slanted elongated germicidal lamp and at least one of the reflector panels are slanted in the same direction.

26. The apparatus of claim 24, wherein the slanted elongated germicidal lamp and at least one of the reflector panels are slanted in opposing directions.

* * * * *